United States Patent [19]

Miller et al.

[11] 4,083,113
[45] Apr. 11, 1978

[54] BRAZING PROCESS FOR ORTHODONTIC ASSEMBLIES

[76] Inventors: Frank R. Miller, 1126 Fairview Ave., Apt. 105, Arcadia, Calif. 91006; Craig A. Andreiko, 517 N. Holliston, Pasadena, Calif. 91106

[21] Appl. No.: 706,037

[22] Filed: Jul. 16, 1976

Related U.S. Application Data

[62] Division of Ser. No. 568,962, Apr. 17, 1975, Pat. No. 3,985,282.

[51] Int. Cl.² .............................................. A61C 7/00
[52] U.S. Cl. ................................................... 32/14 A
[58] Field of Search ........................................ 32/14 A

[56] References Cited

U.S. PATENT DOCUMENTS

| | | | |
|---|---|---|---|
| 3,055,110 | 9/1962 | Kesling | 32/14 A |
| 3,391,461 | 7/1968 | Johnson | 32/14 A |

*Primary Examiner*—Robert Peshock
*Attorney, Agent, or Firm*—Warren T. Jessup

[57] ABSTRACT

A process for making orthodontic assemblies such as brackets and buccal tubes which permits simultaneous heat treating of the assembly while brazing the assembly together. The process consists of assembling a plurality of aligned bases with caps and a brazing insert. The caps are then tack welded (temporarily fastened) to the bases to produce a strip of orthodontic assemblies which can be easily handled. The strips are then heat treated to a brazing temperature in a specified atmosphere. The individual orthodontic assemblies are either automatically separated during the heat treatment or may be easily separated by cutting after removal from the furnace. The bases and caps for the buccal tube assemblies are of a unique design which is readily adaptable to the multiple strip brazing process.

2 Claims, 11 Drawing Figures

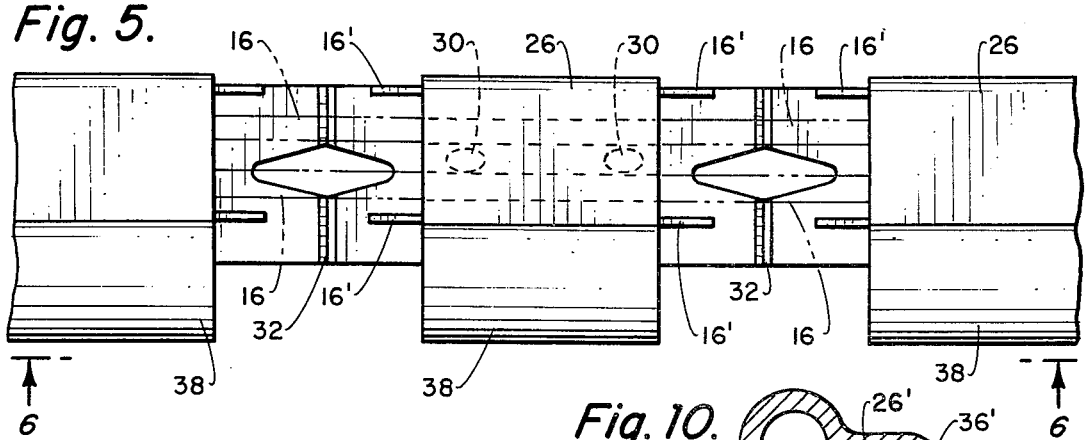
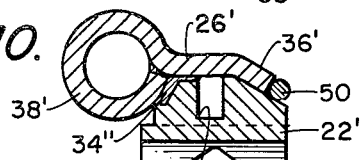
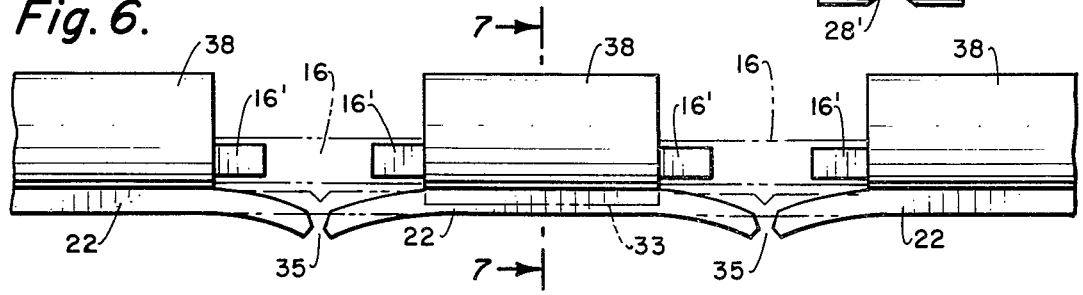
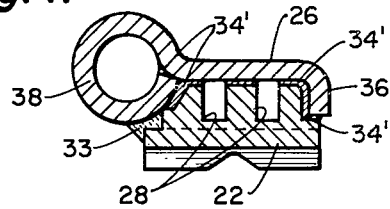
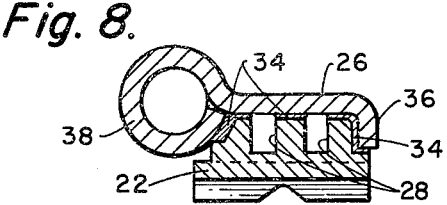
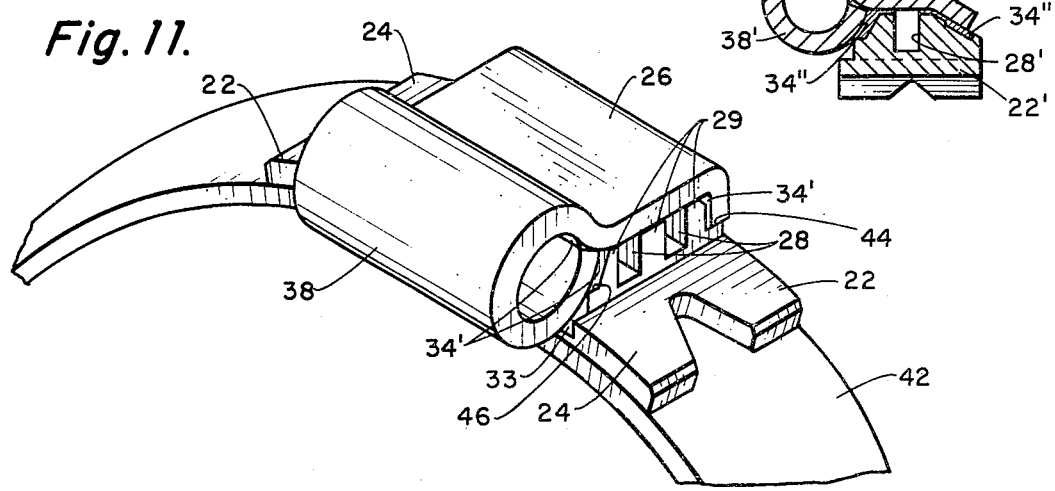

BRAZING PROCESS FOR ORTHODONTIC ASSEMBLIES

This is a division, of application Ser. No. 568,962, filed Apr. 17, 1975 and now U.S. Pat. No. 3,985,202 issued Oct. 12, 1976.

BACKGROUND OF THE INVENTION

This invention relates generally to orthodontic assemblies and more particularly relates to orthodontic assemblies such as brackets and buccal tubes.

Manufacture of orthodontic brackets and buccal tubes has always been difficult because of their small size which makes it difficult to handle them. Thus they do not lend themselves to mass manufacturing techniques. In addition, buccal tubes have been a constant problem to orthodontists because in some cases the forces applied to them cause flaring and wear of the round tube necessitating re-banding of the teeth to replace the worn tube. The wearing is usually caused by the face bow, which is made of a spring tempered stainless steel, harder than the buccal tubes which are usually made of Inconel, a softer material.

Inconel is used because it silver brazes better than stainless steel. Since the Inconel is a relatively soft material, compared to the mating spring wire of the face bow, it wears until the fit is too loose for adequate control of the tooth position. This necessitates replacement of the tube which is very costly and undesirable to the orthodontist and his patient.

To correct the problem and fill this product need, manufacturers have made "heavy-duty" buccal tubes of various designs. The latest is a "cast" tube, rather than a fabricated assembly. Cast tubes are, however, much more costly to manufacture than other designs, and at best heavy-duty buccal tubes cost more to make and therefore sell for approximately double the price of the "standard" buccal tubes.

The invention described herein solves the problem of manufacture and also provides a lighter buccal tube which is greater in strength than prior art devices. The process described permits the buccal tube to be constructed of a strong metal at a reasonable cost and with great strength.

SUMMARY OF THE INVENTION

The purpose of this invention is to permit economical fabrication of large numbers or orthodontic assemblies at a reasonable cost. The novel process is comprised of aligning a plurality of bases for orthodontic assemblies and placing a strip of brazing material along the bases and then positioning an orthodontic component such as a bracket or buccal tube over the strip of brazing material. The bracket or buccal tube cap is then tack welded or otherwise temporarily secured to the base to produce an elongate strip of orthodontic assemblies suitable for heat treating and simultaneous brazing. The entire strip is then placed in a furnace and heated to a temperature which causes the brazing material to fill interstitial spaces between the brackets or buccal tube caps and the base. In one embodiment of the invention the multiple orthodontic assemblies are automatically separated during the brazing process; alternatively the assemblies may be separated after the brazing process by cutting. This method of assembling and brazing a plurality of buccal tubes (or other type of orthodontic device) produces an orthodontic device having greater strength and wear resistance than cast-type tubes. This is because this process permits the use of a stainless steel cap of unique design and heat treatable metallurgy.

While the furnace brazing process is known in industry, it has not been used in the orthodontic manufacturing business because of the high temperatures which are too high for most spring tempered assemblies. In addition, there is the disadvantage of the high temperatures required, necessitating costly and shortlived jigs and fixtures, and the difficulty in handling tiny parts in production. Added to this is the difficulty of placing the tiny brazing alloy "preforms" on the assembly and of keeping the preform in place during the brazing. For this reason it has always been felt that it is more economical to use the tack weld and finish weld assemblies with the spot weld technique. However, the disadvantages of spot welding are that the assemblies are not near as strong as high-temperature brazing or as good looking. Additionally, the procedure is costly and electrode maintenance is a constant problem. Further the quality of the weld constantly changes as the electrodes wear, and the low-temperature brazing alloys corrode and discolor in the mouth.

An important feature of the invention disclosed herein is the provision of an orthodontic assembly having a base with a plurality of upright webs forming at least one channel having a cap resting on the webs which has a cylindrical tube on one side and a flange extending downwardly along the opposite side of one of the webs. The tube and flange portions of the cap form one or more cavities for retaining brazing material between the cap and the base means whereby the orthodontic assembly may be furnace brazed in large quantities.

With the high-temperature brazing of the present invention, stronger orthodontic assemblies of consistent quality can be produced which are chemically clean and bright and will produce less in-mouth corrosion. An additional, not to be overlooked, advantage of this process is the ability to assemble more intricate design configurations economically.

It is one object of the present invention to provide a process of producing orthodontic assemblies which permits large numbers to be produced economically.

Another object of the present invention is to provide a brazing process for orthodontic assemblies in which the assemblies are brazed and heat treated simultaneously.

Yet another object of the present invention is to provide a process of making orthodontic assemblies which are stronger and of consistent quality.

Another object of the present invention is to provide a method of assembling a plurality of orthodontic devices in a strip which can simultaneously be brazed at high temperatures in a furnace.

Still another object of the present invention is to provide a process of manufacturing orthodontic buccal tubes of greater strength and durability at a reduction in cost.

Other objects, advantages and novel features of the invention will become apparent when the following drawings are considered in conjunction with the description.

BRIEF DESCRIPTION OF THE DRAWINGS

FIG. 5 shows the basic strip of FIG. 3 with a plurality of caps attached having a braze alloy in place in preparation for the brazing process.

FIG. 6 is a view of the buccal tube assemblies of FIG. 5 taken at 6—6.

FIG. 7 is a sectional view of one buccal tube assembly taken at 7—7 of FIG. 6.

FIG. 8 is a sectional view of a buccal tube taken at 7—7 of FIG. 6 illustrating the unique design of the buccal tube cap.

FIG. 9 is a sectional view taken at 7—7 of FIG. 6 showing another embodiment.

FIG. 10 is a sectional view similar to FIG. 9.

FIG. 11 illustrates the buccal tube assembly manufactured by the process of the invention described herein attached to a tooth band.

DESCRIPTION OF THE PREFERRED EMBODIMENT

Figure 1:
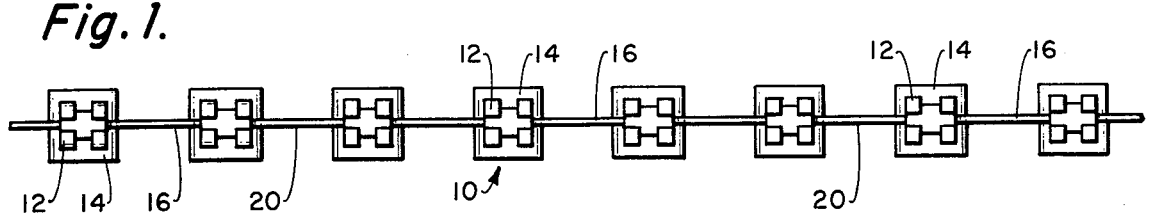
FIG. 1 illustrates a method of assembling a plurality of orthodontic brackets.
Figure 2:
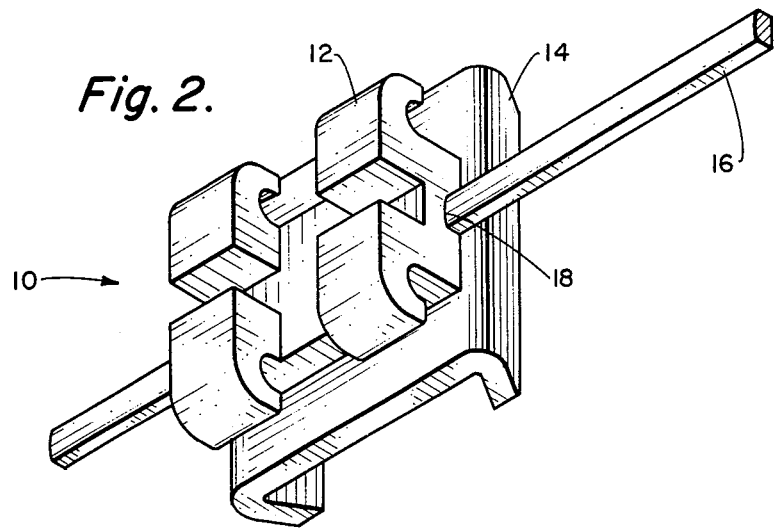
FIG. 2 is an enlarged view of one of the orthodontic brackets assembled by the process of FIG. 1.

Referring now to FIG. 1, there is shown a plurality of orthodontic assemblies assembled together to form a strip prior to furnace brazing. Each individual orthodontic assembly is fabricated in two parts, as shown in FIG. 2 in which the numeral 10 indicates the assembly generally having a bracket 12 and a base 14. The two parts are brazed together by the process of the present invention.

To utilize the process of the present invention a long string of bases 14 are aligned as shown in FIG. 1. A strip of brazing alloy 16 is laid atop the bases 14, and then on top of each base 14 a bracket 12 is positioned. The brazing alloy strip seats in a groove 18 (FIG. 2) formed in the bottom of the bracket 12. While the products are in this position, each bracket 12 is tack (resistance) welded to its base 14, securing the brazing alloy between the bracket 12 and base 14. During this tack welding operation, it is critical that the parts be held in exactly the right relation, but the welding operation itself is easily accomplished since it is only a temporary tack weld.

The strip of brackets shown in FIG. 1 is now large enough to be easily handled and can be placed in a furnace which is heated to heat treating and brazing temperature. As the temperature rises, the strip of brazing alloy 16 parts about midway between each of the assemblies 10, and then flows by capillary action into the flat, interstitial space between the base 14 and the bracket 12, thus effecting a rigid and permanent bond between the two parts. To produce an even distribution of brazing material, the strip 16 may be nicked, notched, or flattened approximately midway between assemblies, as indicated at 20. The strip shown in FIG. 1 is fed into the furnace in untempered condition and the same temperature that effects the brazing is also sufficient to heat treat the metal enough to be satisfactory for the orthodontic purpose required. This double use of the furnace brazing technique is particularly efficacious because if pretempered stainless steel is used, the brazing operation has a tendency to anneal it undesirably and render the product unsatisfactory. To produce the result, a brazing alloy may be chosen which has a fusing temperature which is approximately the same as the temperature required to heat treat the assembly.

Figure 3:
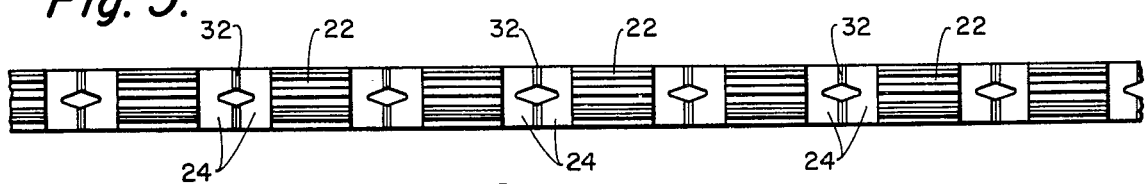
FIG. 3 is a basic strip of preformed bases for manufacturing a plurality of orthodontic assemblies.

A similar process to that described above can be used to make orthodontic assemblies such as buccal tubes. In this process a long string of bases 22 is provided as shown in FIG. 3, joined by flanges 24 which remain intact until after the brazing process is complete. The strips of brazing alloy 16 (FIG. 5) are laid atop the long strip of bases lying in the groove channels 28 formed by webs 29 of the base, and buccal tube caps 26 are attached to each base by tack welding at the center web, as shown at 30. This produces a long strip having multiple buccal tube assemblies ready for the brazing process.

The long strip of bases and caps having the two strips of brazing alloy 16 passing through the channels 28 of the bases is now easily handled and is placed in a furnace which is heated to a heat treating and brazing temperature as before. As the temperature rises, the strips of brazing alloy part and flow by capillary action into the flat interstitial spaces 34', as shown in FIG. 7, between the bases and caps. Since the strip of bases 22 is mechanically joined by flanges 24, the strip of brazing alloy 16 can be pre-cut to controlled lengths, such as is shown at 16', before placing the assemblies in a furnace for brazing, if desired. This produces a rigid and permanent bond between the two products. After the brazing process is complete, the strips are removed from the furnace and the flanges 24 are mechanically severed at the scored portion 32 midway between the bases.

The sectional views of FIGS. 7 through 10 are taken at 7—7 of FIG. 6 and illustrate various embodiments of the invention after the brazing and heat treating process has been completed. In the process of FIG. 7, brazing foil 16' is used and is positioned beneath tube 38 and flange 36, prior to tack welding the additional member or buccal tube cap 26 to the center web of base 22, as shown at 30 (FIG. 5). Ceramic paint 33 may be applied underneath the tubular portion 38 of cap 26 to confine the brazing material during the brazing process, if desired. When the assemblies are heated to the fuse temperature of the brazing material, it flows into the spaces 34', welding the cap to the base.

An alternative method of making the buccal tube assemblies of FIG. 5 is shown in FIG. 8. In this method the assembly is the same as before, except that instead of using a brazing alloy in the form of a foil, a wire or rod is used in the channels 28 beneath the tube and base for attaching the buccal tube cap 26 to the webs 29. The finished assembly of FIG. 8 is substantially the same as that of FIG. 7 with the wire or rod of brazing material filling voids 34. In both of the latter two methods the brazing alloy wire or rod and the brazing foil may be chopped near each base before the brazing process takes place, because the bases are held in an aligned fashion mechanically by flanges 24.

The brazing process described preferably takes place in a dry hydrogen atmosphere or vacuum at temperatures exceeding the melting point of the brazing alloy and which are also sufficient to anneal or heat treat the assemblies. Preferably the heat treating temperature and brazing temperature are within a range in which one phenomenon is not detrimental to the other. That is, the melting point of the brazing alloy and the heat treating temperature are mutually compatible.

To produce these devices the bases are fabricated in long metal strips with each base having a plurality of webs 29 forming dual channels 28, and joined by flanges 24 which are severed or cut after the brazing process is complete, as was discussed previously.

Figure 4:
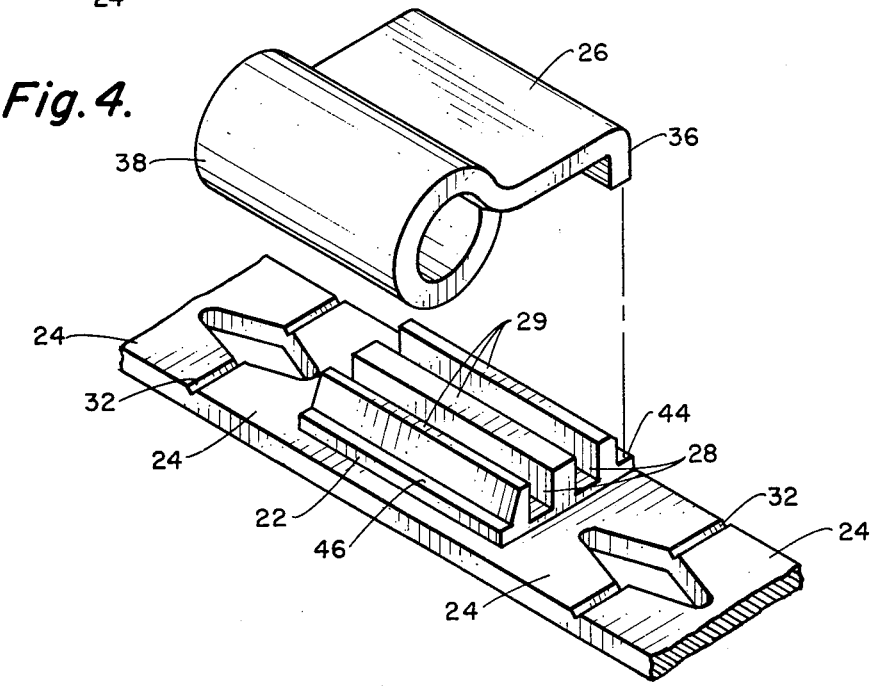
FIG. 4 is a detailed perspective drawing of the buccal tube cap for use with the basic strip of FIG. 3.

The buccal tube cap 26 is of a novel stamped type, shown in FIG. 4, having a round tube 38 formed at one side and a flange or lip 36 at the opposite side which fit over the webs 29, as shown in FIG. 7. The cap 26 preferably is made of a durable (hard) stainless steel which is heat treated and brazed simultaneously in a controlled temperature and atmosphere of dry hydrogen or vacuum. The novel buccal tube cap 26 design is fabricated by die stamping in several steps. Manufacturing cost of producing the assemblies by this process and design is reduced over cast-type buccal tubes, and strength and wear resistance are greater. Preferably the base 22 is constructed of a more flexible (softer) stainless steel than the caps 26, and is of non-heat hardenable material. An additional benefit of this design and process is that the size and bulk are less than previous similar devices.

FIGS. 9 and 10 illustrate embodiments having a single channel 28 formed by the webs. In FIG. 9 the cap 26' has a flange 36' which is only bent at a slight angle to hold the brazing alloy in place. During the heat treating and brazing, the soldering material flows by capillary action into voids 34". The embodiment of FIG. 10 is the same as in FIG. 9, except that a rod 50 of brazing alloy is tacked to the assembly along the edge of flange 36' rather than being held beneath the flange.

FIG. 11 illustrates a complete assembly for placement on a tooth for use in conjunction with a face bow of a conventional headgear. Force is applied to the teeth through the round tube 38 of the buccal tube cap 26 and the mating spring wire of the face bow. The buccal tube assembly indicated generally in FIG. 11 is attached to a tooth band or collar 42 by welding or any other suitable process.

In all cases the amount of brazing alloy 16 or 16' is controlled by the spacing of the assemblies of FIG. 1 or by cutting the brazing alloy to predetermined lengths. This step provides just the right amount of brazing material to fill the interstitial spaces between the bases and the orthodontic components, such as the brackets or buccal tubes.

Whereas the present invention has been shown and described herein in what is conceived to be the best mode contemplated, it is recognized that departures may be made therefrom within the scope of the invention which is therefore not to be limited to the details disclosed herein but is to be afforded the full scope of the invention.

What is claimed is:

1. An orthodontic assembly comprising:
   base means having a plurality of upright webs forming at least one channel;
   a cap resting on and secured to the top of said webs for enclosing said one or more channels;
   said cap terminating on one side in a cylindrical tube and on the other side in a downwardly extending flange;
   said tube and said flange forming with said webs a cavity for retaining brazing material whereby said assembly may be furnace brazed.

2. An orthodontic assembly according to claim 1 wherein:
   said upright web forms two channels; and
   the outside edges of said web are adapted to form channels with said cap for securing said brazing material.

* * * * *